(12) United States Patent
Liu et al.

(10) Patent No.: US 12,171,864 B2
(45) Date of Patent: Dec. 24, 2024

(54) BIOLOGICAL SELF-ASSEMBLED NANOCRYSTAL INJECTION HAVING A LYMPHATIC TARGETING FUNCTION AND PREPARATION METHOD

(71) Applicant: SHENZHEN CHINA RESOURCES JIUCHUANG MEDICAL AND PHARMACEUTICAL CO., LTD, Shenzhen (CN)

(72) Inventors: Jun Liu, Liaoning (CN); Tiantian Ye, Liaoning (CN); Dan Zhang, Liaoning (CN)

(73) Assignee: SHENZHEN CHINA RESOURCES JIUCHUANG MEDICAL AND PHARMACEUTICAL CO., LTD, Shenzhen (CN)

( * ) Notice: Subject to any disclaimer, the term of this patent is extended or adjusted under 35 U.S.C. 154(b) by 861 days.

(21) Appl. No.: 16/482,054

(22) PCT Filed: Sep. 15, 2017

(86) PCT No.: PCT/CN2017/101801
§ 371 (c)(1),
(2) Date: Jul. 30, 2019

(87) PCT Pub. No.: WO2018/233095
PCT Pub. Date: Dec. 27, 2018

(65) Prior Publication Data
US 2020/0163872 A1 May 28, 2020

(30) Foreign Application Priority Data
Jun. 23, 2017 (CN) .......................... 201710486510.8

(51) Int. Cl.
| | | |
|---|---|---|
| *A61K 9/00* | (2006.01) | |
| *A61K 9/51* | (2006.01) | |
| *A61K 31/136* | (2006.01) | |
| *A61K 47/10* | (2017.01) | |
| *A61K 47/12* | (2006.01) | |
| *A61K 47/14* | (2017.01) | |
| *A61K 47/26* | (2006.01) | |
| *B82Y 5/00* | (2011.01) | |

(52) U.S. Cl.
CPC .............. *A61K 9/0019* (2013.01); *A61K 9/51* (2013.01); *A61K 9/5192* (2013.01); *A61K 31/136* (2013.01); *A61K 47/10* (2013.01); *A61K 47/12* (2013.01); *A61K 47/14* (2013.01); *A61K 47/26* (2013.01); *B82Y 5/00* (2013.01)

(58) Field of Classification Search
CPC ...... A61K 9/0019; A61K 9/51; A61K 9/5192; A61K 31/136; A61K 47/10; A61K 47/12; A61K 47/14; A61K 47/26; A61K 47/183; A61K 47/36; A61K 9/19; B82Y 5/00; A61P 35/04; A61P 7/00
See application file for complete search history.

(56) References Cited

U.S. PATENT DOCUMENTS 6,143,795 A    11/2000  Moschner et al.

FOREIGN PATENT DOCUMENTS

| CN | 1298310 A | 6/2001 |
| CN | 1602844 A | 4/2005 |
| CN | 1242740 C | 2/2006 |
| CN | 102397561 A | 4/2012 |
| CN | 106267240 A | 1/2017 |
| CN | 107149592 A | 9/2017 |

OTHER PUBLICATIONS

English machine translation of CN 102397561 A—Apr. 4, 2012—23 pages (Year: 2012).*
International Search Report issued for corresponding International Application No. PCT/CN2017/101801 mailed Mar. 23, 2018.
European Patent Office Extended Search Report for Application No. 17915174.1 dated Feb. 17, 2021 (7 pages).
Office Action from the Intellectual Property Office of the People's Republic of China for Application No. 201710486510.8 dated Dec. 19, 2018 (8 pages).
Office Action from the Intellectual Property Office of the People's Republic of China for Application No. 201710486510.8 dated Jan. 31, 2019 (10 pages).
Office Action from the Intellectual Property Office of the People's Republic of China for Application No. 201710486510.8 dated Apr. 9, 2019 (9 pages).
European Patent Office Examination Report for Application No. 17915174.1 dated Jan. 19, 2023 (6 pages).

(Continued)

*Primary Examiner* — Aradhana Sasan
(74) *Attorney, Agent, or Firm* — Michael Best & Friedrich LLP

(57) ABSTRACT

A biological self-assembled nanocrystal injection having a lymphatic targeting function and an administration method for targeting a lymphatic system using the biological self-assembled nanocrystal injection. The injection comprises 0.05-5% of mitoxantrone and a salt thereof, 0.1-10% of an osmotic pressure regulator, 0.001-0.1% of a buffering agent, 0.01-0.1% of an antioxidant, 0.05-1% of an adsorbent, and 0-20% of a filler. The administration method is interstitial injection, and a lymph node will produce a blue color visible to the naked eye after passive targeting to the lymphatic system.

12 Claims, No Drawings

(56) References Cited

OTHER PUBLICATIONS

Vietnam Patent Office Action for Application No. 1-2019-06268 dated Jan. 17, 2022 (4 pages).
Philippines Patent Office Action for Application No. 1/2019/502480 dated Sep. 11, 2023 (4 pages).
Vietnamese Patent Office Action for Application No. 1-2019-06268 dated May 27, 2024 (4 pages).
Malaysian Patent Office Action for Application No. PI2019006523 dated Apr. 18, 2024 (3 pages).
Thailand Patent Office Action for Application No. 1901006975 dated Apr. 17, 2024 (8 pages including English translation).

* cited by examiner

BIOLOGICAL SELF-ASSEMBLED NANOCRYSTAL INJECTION HAVING A LYMPHATIC TARGETING FUNCTION AND PREPARATION METHOD

CROSS REFERENCE TO RELATED APPLICATIONS

This application is a national stage filing under 35 U.S.C. § 371 of International Patent Application No.: PCT/CN2017/101801, filed Sep. 15, 2017, which claims priority to Chinese Patent Application No. 201710486510.8, filed Jun. 23, 2017, the entire contents of all of which are hereby incorporated by reference herein.

TECHNICAL FIELD

The present application relates to design and preparation of a new dosage form having a lymphatic targeting function, and provides a formulation composition and preparation method of an in vivo self-assembled nanocrystal injection.

BACKGROUND

Lymphatic metastasis is one of the important factors affecting the prognosis of malignant tumors. Tumor cells can enter the lymphatic system and diffuse at an early stage, and enter the non-affected lymph nodes or lymph nodes away from the primary tumor through the lymphatic collateral circulation, forming a so-called skip metastasis and limiting the application of surgery. Regional lymph nodes are less sensitive to radiotherapy than primary tumors, and systemic chemotherapy is not effective for metastatic lymph nodes, because chemotherapeutic drugs in conventional dosage forms are not easily transported to lymph nodes. Since the efficacy of treating lymph node metastases directly affects the cure rate and survival rate of patients, the targeting of lymph node metastases is receiving more and more attention. Lymph nodes have become a very promising target organ in tumor chemotherapy.

Novel drug delivery systems have been designed to enable lymphatic targeting by use of the characteristic that macromolecular substances and particles are easily phagocytosed by the lymphatic system. At present, the drug carriers used include emulsions, activated carbon, cyclodextrin, liposomes, microspheres, dendrimers, nanocrystals, etc., and they are combined with chemotherapeutic drugs or imaging substances by chemical bonds, emulsification, adsorption, inclusion, encapsulation, etc. Although these drug carriers have significant lymphatic targeting properties compared to small molecule drugs, they are inferior in terms of in vitro storage stability and in vivo dilution stability, and their ability to maintain effective drug loading and carrier integrity in physiological environments is also unclear.

Nanocrystals, also known as nanocrystallines or nanosuspensions, are submicron colloidal dispersions prepared by self-assembling or pulverization techniques with a small amount of surfactant or polymer as a stabilizer, and having the particle size between 1 and 100 nm, and thus also having a good lymphatic targeting function. Compared with other drug delivery systems, nanocrystals are directly formed from drugs, and have the advantages of high drug loading, easy industrial production, and relatively low preparation cost. They can also be administered by various drug delivery routes, such as subcutaneous injection, intravenous injection, oral administration, transdermal administration, and the like.

The nanocrystals themselves have relatively high activity and are very unstable. When certain activation conditions are met, they will release excess free energy, and the particles will grow up, resulting in the loss of the characteristics of the nanomaterial. At present, there are two basic processes: bottom-up (in vitro self-assembling technology) and top-down (crushing technology), for the preparation of drug nanocrystals. Because there are some insurmountable defects in the in vitro self-assembling technology, such as organic solvent residues, poor physical stability of formulation, tendency to Ostwald ripening, etc., the crushing technology is more widely used in the pharmaceutical industry. However, due to the large amount of energy generated during the crushing process, crystal form transformation may occur. Therefore, compared with other drug delivery systems, nanocrystals also have the disadvantages of poor stability in vitro, difficulties in controlling stability in vivo, susceptibility of formulation stability to preparation techniques, and difficulties in scaling up. Therefore, the preparation of nanocrystals is difficult, which hinders their clinical application.

For the above-mentioned novel drug delivery system having a lymphatic targeting function, the administration mode can be selected from the group consisting of tissue interstitial administration, mucosal administration, vascular administration, digestive tract administration, etc. Among them, the tissue interstitial administration is also called interstitial administration. The tissue interstitial administration, such as subcutaneous, intramuscular, peritumoral, and intratumoral administration, of the drug delivery system is accompanied by its transport and uptake by capillary blood vessels and capillary lymphatic vessels. Due to the loose connection between endothelium cells, there are often many open gaps. The drug-loading system can enter capillary lymphatic vessels through the gaps between endothelium cells of the vessels and by the pinocytosis and phagocytosis of the endothelial cells, and then reach the regional lymph nodes through lymphatic drainage. Due to the advantages of this mode of administration in lymphatic targeting, it has become the most common mode of administration for drug delivery systems with a lymphatic targeting function. To date, the FDA has approved three formulations for lymphatic targeting: Sulfur Colloid approved in 1974, Isosulfan Blue approved in 1981, and Lymphoseek approved in 2013. In China, only the nano-carbon suspension injection (Kanalin) of Chongqing Laimei Pharmaceutical Co., Ltd. was approved for marketing. The intratumoral or peritumoral tissue interstitial administration is selected as the mode of administration for all the four marketed formulations having lymphatic targeting functions.

Mitoxantrone is a research reagent widely used in molecular biology, pharmacology and other scientific research. It is also an antibiotic-type antitumor drug. It has a structure and anticancer effect similar to doxorubicin, has no amino sugar structure, does not generate free radicals, and has the inhibitory effect on lipid peroxidation. It can kill tumor cells at any stage of cell cycle, with both proliferating and non-proliferating cells inhibited, so it has anti-tumor activity comparable with or slightly higher than doxorubicin and significantly higher than cyclophosphamide, Fluorouracil, methotrexate, vincristine and cytosine arabinoside and a broad anti-cancer spectrum. The drug substance powder and the solution of mitoxantrone both have a color. The drug substance is a purple-brown powder in appearance, dark blue in an aqueous solution, and dark purple-red in concentrated sulfuric acid. The mitoxantrone hydrochloride for injection on the market is a solution administered by the route of intravenous injection, and its indications are mainly for malignant lymphoma, breast cancer and acute leukemia. There are no pharmaceutical formulations of mitoxantrone or a salt thereof having a lymphatic targeting function on both the domestic and foreign market.

SUMMARY OF THE INVENTION

The technical problem solved by the present application is to provide a formulation composition, a preparation method, an administration mode, and a design principle of a solution-type injection capable of biologically self-assembling into nanocrystals in vivo.

This application is implemented by the following technical solutions:

A biological self-assembled nanocrystal injection having a lymphatic targeting function, the components of which comprise 0.05% to 5% of mitoxantrone or a salt thereof and 0.1 to 10% of an osmotic pressure regulator calculated by a mass-to-volume ratio (g/mL), with the remainder being a solvent.

Optionally, the injection further comprises 0.01 to 0.1% of a buffer, 0.01 to 0.1% of an antioxidant, 0.05 to 1% of an adsorbent, and 0 to 20% of a filler.

Optionally, the mitoxantrone or salt thereof is present in a concentration ranging from 0.1% to 1% in the injection.

The pH range of the injection is from 2.0 to 6.0.

Optionally, the pH range of the injection is from 3.5 to 5.5

The osmotic pressure of the injection ranges from 285 to 2317 mmol/Kg.

Optionally, the osmotic pressure of the injection ranges from 307 to 1503 mmol/Kg.

Optionally, the salt of mitoxantrone is one or more selected from the group consisting of hydrochloride, oxalate, sulfate, phosphate, acetate, or citrate of mitoxantrone.

The particle size of biological self-assembled nanocrystals ranges from 1 to 1000 nm under physiological conditions.

Optionally, the particle size of biological self-assembled nanocrystals ranges from 10 to 100 nm under physiological conditions.

Optionally, the particle size of biological self-assembled nanocrystals ranges from 30 to 60 nm under physiological conditions.

Optionally, the injection comprises a small-volume aqueous injection and a powder injection, with the small-volume aqueous injection containing no filler and the powder injection containing a filler in an amount of greater than 0 and less than or equal to 20%.

Optionally, the osmotic pressure regulator is selected from the group consisting of sodium chloride, glucose, sorbitol, mannitol, glycerin, PEG, phosphate, citrate, or combinations thereof.

Optionally, the buffer is one or more selected from the group consisting of acetic acid, sodium acetate, citric acid, or sodium citrate.

Optionally, the antioxidant is one or more selected from the group consisting of sodium sulfite, sodium hydrogen sulfite, sodium metasulfite, sodium thiosulfate, or disodium edetate.

Optionally, the filler is one or more selected from the group consisting of a monosaccharide, i.e. glucose, fructose, galactose, ribose, or deoxyribose, a disaccharose, i.e. sucrose, trehalose, maltose, or lactose, or a polymeric sugar, i.e. mannitol, sorbitol, lactitol, xylitol, maltitol, or erythritol.

Optionally, the adsorbent is activated carbon.

Optionally, after the lymphatic targeting function is realized, the lymph nodes produce a blue color visible to the naked eyes.

Optionally, after the lymphatic targeting function is realized, the tumor metastasis lymph nodes shrink or return to normal size.

Optionally, the administered injection is in the form of a solution, and the mitoxantrone or its salt is present in the form of completely dissolved molecules.

Optionally, after the injection in the form of a solution is administered interstitially, the nanocrystals are self-assembled in the injection site.

Optionally, the mode of administration to realize the lymphatic targeting function is by interstitial injection.

Optionally, the mode of administration is selected from the group consisting of subcutaneous, muscular, muscular, submucosal, intraperitoneal, intra-tissue, or peri-tissue interstitial injection or combinations thereof.

A preparation method of biological self-assembled nanocrystal injection having a lymphatic targeting function, the injection being a small-volume aqueous biological self-assembled nanocrystal injection, comprising the following preparation steps: weighing an appropriate amount of raw materials and excipients, adding 70% of the prescribed amount of water for injection to a concentrated mixing tank, adding the prescribed amount of excipients, stirring for about 15 minutes to dissolve, then adding mitoxantrone or a salt thereof, stirring for about 20 minutes to dissolve, feeding the activated carbon, stirring for adsorption for 20 minutes at 40 to 60° C., filtering the concentrated solution through a 3 μm stainless steel pleated cartridge filter and transferring it into a dilution tank, supplementing water for injection to the total amount of the solution to be prepared, stirring for 10 minutes, filtering the drug solution through two sterilizing filters with pore size of 0.22 μm in series, and aseptically and separately filling and sealing.

Alternatively, the injection is a biological self-assembled nanocrystal powder injection, and the method comprises the following preparation steps: weighing an appropriate amount of raw materials and excipients, adding 70% of the prescribed amount of water for injection to a concentrated mixing tank, adding the prescribed amount of excipients, stirring for about 15 minutes to dissolve, then adding mitoxantrone or a salt thereof, stirring for about 20 minutes to dissolve, feeding the activated carbon, stirring for adsorption for 20 minutes at 40 to 60° C., filtering the concentrated solution through a 3 μm stainless steel pleated cartridge filter and transferring it into a dilution tank, supplementing water for injection to the total amount of the solution to be prepared, stirring for 10 minutes, filtering the drug solution through two sterilizing filters with pore size of 0.22 μm in series, adding mannitol to be dissolved, and removing water by freeze-drying to obtain a biological self-assembled nanocrystal freeze-dried powder for injection, which can be administered by interstitial injection after hydration and shaking prior to use, with the hydration medium being one or more selected from the group consisting of water for injection, physiological saline, and glucose injection.

The mass-to-volume percentages in this application are all expressed by g/mL.

In the present application, mitoxantrone hydrochloride is selected as the active ingredient of the biological self-assembled nanocrystals, and the mitoxantrone hydrochloride is present in the form of a well water-soluble hydrochloride in the acidic condition formed by the preparation of the product.

(1) The pH value of the acidic condition has a key influence on the behavior of the injection of self-assembling into nanocrystals in vivo. When the injection has a pH ranging from 2.0 to 6.0 and is administered by interstitial injection, with the interstitial site characterized by the presence of a body fluid of pH 7.4, the mitoxantrone hydrochloride is returned to mitoxantrone as the hydrochloride moiety is neutralized in the physiological pH environment, and thereby the solubility is lowered to cause precipitation of nanocrystals. When the pH of the injection is less than 2.0, the body fluid of pH 7.4 cannot achieve neutralization, and therefore the nanocrystals cannot be effectively produced. When the pH of the injection is greater than 6.0, the injection is unstable and the mitoxantrone hydrochloride precipitates, affecting the quality of the injection. Through effective optimization of the formulation, it is determined that when the pH of the injection ranges from 3.5 to 5.5, the neutralization of the body fluid of pH 7.4 is the most effective, enabling the rapid formation of a large number of nanocrystals in the interstitial site to reach the lymphatic targeting function.

(2) Since the amount of body fluid in the interstitial site is small, the concentration of the drug administered significantly affects the amount and rate of formation of the nanocrystals. The optimal concentration range of administration in the present application is 0.05-5% (g/mL, W: V). When the concentration of administration is lower than the range, it is difficult to form nanocrystals with targeting ability under physiological conditions after interstitial injection. When the concentration of administration is higher than the range, toxic side effects on the lymphatic system will occur.

(3) The circulation rate of body fluid in the interstitial site is slow. The drug injected in the interstitial site is motivated to enter the lymphatic system mainly by the difference in osmotic pressure between the interstitial site and the lymphatic system. The hypotonic injection is not conducive to the drug drainage to lymphatic system through the gaps in the capillary lymphatic vessels, so the isotonic or somewhat hypertonic injection is beneficial to the lymphatic drainage of the self-assembled nanocrystals. The suitable osmotic pressure range in this application is from 285 to 2317 mmol/Kg, and the optimal osmotic pressure range is from 307 to 1503 mmol/Kg. When the osmotic pressure is less than 285 mmol/Kg, the motivation of lymphatic drainage is insufficient, and when the osmotic pressure is greater than 2317 mmol/Kg, the concentration of osmotic pressure regulator is too high in the injection, causing irritation in the injection site.

The body fluid in the interstitial injection site is small in amount, has the pH value of 7.4, and circulates slowly. It is because of such characteristics of physiological conditions that with an appropriate pH of the injection, an appropriate concentration of administration and an appropriate osmotic pressure, the water solubility is lowered after the hydrochloride moiety is removed from mitoxantrone hydrochloride, resulting in self-assembling of nanocrystals with particle size greater than 30 nm and less than 60 nm in the interstitial site. There are certain overlapped gaps between the endothelial cells of the lymphatic vessels. Small molecule drugs and nanoparticles with particle size of less than 20 nm will produce a diffusion effect in the injection site after subcutaneous injection, while those with particle size from 20 nm to 100 nm can pass through the endothelial cell gaps of lymphatic vessels and produce a good lymphatic targeting effect.

MODE OF CARRYING OUT THE INVENTION

Example 1

The formulation of small-volume aqueous biological self-assembled nanocrystal injection and the amounts of components for 1000 injections were as follows:

| | |
|---|---|
| Mitoxantrone hydrochloride | 11.64 g |
| Acetic acid | 0.92 g |
| Sodium acetate | 0.10 g |
| Water for injection | 2000 mL |

An appropriate amount of raw materials and excipients were weighed. 70% of the prescribed amount of water for injection was added to a concentrated mixing tank. The prescribed amount of excipients were added and dissolved by stirring for about 15 minutes. Then, mitoxantrone hydrochloride was added and dissolved by stirring for about 20 minutes.

The small-volume aqueous biological self-assembled nanocrystal injection prepared from the formulation and process comprised mitoxantrone hydrochloride in a concentration of 0.58%, and had a pH determined to be 3.5 and osmotic pressure of 196 mmol/Kg. The self-assembled nanocrystals under the interstitial biological conditions had a particle size of 50 nm. The first class of metastatic lymph nodes after subcutaneous interstitial administration produced a dark blue color visible to naked eyes, and the second and third classes of lymph nodes produced a light blue color visible to naked eyes. The weight and volume of metastatic lymph nodes of each class decreased significantly or returned to normal and there was no significant toxicity for the injection site or the lymphocytes.

Example 2

The formulation of small-volume aqueous biological self-assembled nanocrystal injection and the amounts of components for 1000 injections were as follows:

| | |
|---|---|
| Mitoxantrone hydrochloride | 11.64 g |
| Sodium chloride | 16.0 g |
| Acetic acid | 0.92 g |
| Sodium acetate | 0.10 g |
| Disodium edetate | 0.10 g |
| Water for injection | 2000 mL |
| Activated carbon (used in the process and finally removed) | 2 g |

An appropriate amount of raw materials and excipients were weighed. 70% of the prescribed amount of water for injection was added to a concentrated mixing tank. The prescribed amount of excipients were added and dissolved by stirring for about 15 minutes. Then, mitoxantrone hydrochloride was added and dissolved by stirring for about 20 minutes. The activated carbon was fed and stirred for adsorption for 20 minutes at 40 to 60° C. The concentrated solution was filtered through a 3 μm stainless steel pleated cartridge filter and transferred into a dilution tank, supplemented with water for injection to the total amount of the solution to be prepared and stirred for 10 minutes. The drug solution was filtered through two sterilizing filters (with pore size of 0.22 μm) in series, aseptically and separately filled, and sealed.

The small-volume aqueous biological self-assembled nanocrystal injection prepared from the formulation and process comprised mitoxantrone hydrochloride in a concentration of 0.57%, and had a pH determined to be 3.5 and osmotic pressure of 938 mmol/Kg. The self-assembled nanocrystals under the interstitial biological conditions had a particle size of 50 nm. The first, second, and third classes of metastatic lymph nodes after subcutaneous interstitial administration produced a dark blue color visible to naked eyes. The weight and volume of metastatic lymph nodes of each class decreased significantly or returned to normal and there was no significant toxicity for the injection site or the lymphocytes.

Example 3

The formulation of small-volume aqueous biological self-assembled nanocrystal injection and the amounts of components for 1000 injections were as follows:

| | |
|---|---|
| Mitoxantrone oxalate | 1.164 g |
| Glucose | 80.00 g |
| Citric acid | 1.84 g |
| Sodium citrate | 0.20 g |
| Sodium sulfite | 0.20 g |
| Water for injection | 2000 mL |
| Adsorbent (used in the process and finally removed) | 2 g |

An appropriate amount of raw materials and excipients were weighed. 70% of the prescribed amount of water for injection was added to a concentrated mixing tank. The prescribed amount of excipients were added and dissolved by stirring for about 15 minutes. Then, mitoxantrone oxalate was added and dissolved by stirring for about 20 minutes. The activated carbon was fed and stirred for adsorption for 20 minutes at 40 to 60° C. The concentrated solution was filtered through a 3 μm stainless steel pleated cartridge filter and transferred into a dilution tank, supplemented with water for injection to the total amount of the solution to be prepared and stirred for 10 minutes. The drug solution was filtered through two sterilizing filters (with pore size of 0.22 μm) in series, aseptically and separately filled, and sealed.

The small-volume aqueous biological self-assembled nanocrystal injection prepared from the formulation and process comprised mitoxantrone oxalate in a concentration of 0.056%, and had a pH determined to be 5.5 and osmotic pressure of 1503 mmol/Kg. The self-assembled nanocrystals under the interstitial biological conditions had a particle size of 40 nm. The first, second, and third classes of metastatic lymph nodes after subcutaneous interstitial administration produced a light blue color visible to naked eyes. The weight and volume of metastatic lymph nodes of each class decreased to a certain degree and there was no significant toxicity for the injection site or the lymphocytes.

Example 4

The formulation of small-volume aqueous biological self-assembled nanocrystal injection and the amounts of components for 1000 injections were as follows:

| | |
|---|---|
| Mitoxantrone sulfate | 116.40 g |
| Glycerin | 20.13 g |
| Acetic acid | 0.92 g |
| Sodium acetate | 0.10 g |
| Sodium metasulfite | 0.40 g |
| Water for injection | 2000 mL |
| Adsorbent (used in the process and finally removed) | 2 g |

An appropriate amount of raw materials and excipients were weighed. 70% of the prescribed amount of water for injection was added to a concentrated mixing tank. The prescribed amount of excipients were added and dissolved by stirring for about 15 minutes. Then, mitoxantrone sulfate was added and dissolved by stirring for about 20 minutes. The activated carbon was fed and stirred for adsorption for 20 minutes at 40 to 60° C. The concentrated solution was filtered through a 3 μm stainless steel pleated cartridge filter and transferred into a dilution tank, supplemented with water for injection to the total amount of the solution to be prepared and stirred for 10 minutes. The drug solution was filtered through two sterilizing filters (with pore size of 0.22 μm) in series, aseptically and separately filled, and sealed.

The small-volume aqueous biological self-assembled nanocrystal injection prepared from the formulation and process comprised mitoxantrone sulfate in a concentration of 5.44%, and had a pH determined to be 3.5 and osmotic pressure of 307 mmol/Kg. The self-assembled nanocrystals under the interstitial biological conditions had a particle size of 60 nm. The first, second, and third classes of metastatic lymph nodes after subcutaneous interstitial administration produced a dark blue color visible to naked eyes. The weight and volume of metastatic lymph nodes of each class returned to normal and there was significant toxicity for the injection site and the lymphocytes.

Example 5

The formulation of biological self-assembled nanocrystal powder injection and the amounts of components for 1000 injections were as follows:

| | |
|---|---|
| Mitoxantrone hydrochloride | 11.64 g |
| Mannitol | 16.0 g |
| Acetic acid | 0.92 g |
| Sodium acetate | 0.10 g |
| Disodium edetate | 0.10 g |
| Mannitol | 200 g |
| Water for injection | 2000 mL |
| Activated carbon (used in the process and finally removed) | 2 g |

The preparation process was as follows:
An appropriate amount of raw materials and excipients were weighed. 70% of the prescribed amount of water for injection was added to a concentrated mixing tank. The prescribed amount of excipients except the filler were added and dissolved by stirring for about 15 minutes. Then, mitoxantrone hydrochloride was added and dissolved by stirring for about 20 minutes. The activated carbon was fed and stirred for adsorption for 20 minutes at 40 to 60° C. The concentrated solution was filtered through a 3 μm stainless steel pleated cartridge filter and transferred into a dilution tank, supplemented with water for injection to the total amount of the solution to be prepared and stirred for 10 minutes. The drug solution was filtered through two sterilizing filters (with pore size of 0.22 μm) in series. Mannitol was added and dissolved. Water was removed by freeze-drying to obtain a biological self-assembled nanocrystal freeze-dried powder for injection, which can be administered by interstitial injection after hydration and shaking prior to use.

The biological self-assembled nanocrystal powder injection prepared from the formulation and process had a smooth surface without collapse and shrinkage after freeze-drying. After the hydration with water for injection, the mitoxantrone hydrochloride injection was formed, which comprised mitoxantrone hydrochloride in a concentration of 0.52% and had a pH determined to be 3.5 and osmotic pressure of 938 mmol/Kg. The self-assembled nanocrystals under the interstitial biological conditions had a particle size of 40 nm. The first, second, and third classes of metastatic lymph nodes after subcutaneous interstitial administration produced a dark blue color visible to naked eyes. The weight and volume of metastatic lymph nodes of each class decreased significantly or returned to normal and there was no significant toxicity for the injection site or the lymphocytes.

Example 6

The formulation of biological self-assembled nanocrystal powder injection and the amounts of components for 1000 injections were as follows:

| | |
|---|---|
| Mitoxantrone phosphate | 11.64 g |
| Sorbitol | 8.0 g |
| Citric acid | 0.74 g |
| Sodium citrate | 0.30 g |
| Disodium edetate | 0.10 g |
| Sucrose | 300 g |
| Water for injection | 2000 mL |
| Activated carbon (used in the process and finally removed) | 2 g |

The preparation process was as follows:

An appropriate amount of raw materials and excipients were weighed. 70% of the prescribed amount of water for injection was added to a concentrated mixing tank. The prescribed amount of excipients except the filler were added and dissolved by stirring for about 15 minutes. Then, mitoxantrone phosphate was added and dissolved by stirring for about 20 minutes. The activated carbon was fed and stirred for adsorption for 20 minutes at 40 to 60° C. The concentrated solution was filtered through a 3 μm stainless steel pleated cartridge filter and transferred into a dilution tank, supplemented with water for injection to the total amount of the solution to be prepared and stirred for 10 minutes. The drug solution was filtered through two sterilizing filters (with pore size of 0.22 μm) in series. Sucrose was added and dissolved. Water was removed by freeze-drying to obtain a biological self-assembled nanocrystal freeze-dried powder for injection, which can be administered by interstitial injection after hydration and shaking prior to use.

The biological self-assembled nanocrystal powder injection prepared from the formulation and process had collapse and shrinkage in the surface after freeze-drying. After the hydration with water for injection, the mitoxantrone phosphate injection was formed, which comprised mitoxantrone phosphate in a concentration of 0.499% and had a pH determined to be 5.5 and osmotic pressure of 307 mmol/Kg. The self-assembled nanocrystals under the interstitial biological conditions had a particle size of 55 nm. The first, second, and third classes of metastatic lymph nodes after subcutaneous interstitial administration produced a dark blue color visible to naked eyes. The weight and volume of metastatic lymph nodes of each class decreased significantly or returned to normal and there was no significant toxicity for the injection site or the lymphocytes.

Example 7

The formulation of biological self-assembled nanocrystal powder injection and the amounts of components for 1000 injections were as follows:

| | |
|---|---|
| Mitoxantrone acetate | 11.64 g |
| PEG 400 | 30.0 g |
| Acetic acid | 0.92 g |
| Sodium acetate | 0.10 g |
| Disodium edetate | 0.10 g |
| Trehalose | 200 g |
| Water for injection | 2000 mL |
| Activated carbon (used in the process and finally removed) | 2 g |

The preparation process was as follows:

An appropriate amount of raw materials and excipients were weighed. 70% of the prescribed amount of water for injection was added to a concentrated mixing tank. The prescribed amount of excipients except the filler were added and dissolved by stirring for about 15 minutes. Then, mitoxantrone acetate was added and dissolved by stirring for about 20 minutes. The activated carbon was fed and stirred for adsorption for 20 minutes at 40 to 60° C. The concentrated solution was filtered through a 3 μm stainless steel pleated cartridge filter and transferred into a dilution tank, supplemented with water for injection to the total amount of the solution to be prepared and stirred for 10 minutes. The drug solution was filtered through two sterilizing filters (with pore size of 0.22 μm) in series. Trehalose was added and dissolved. Water was removed by freeze-drying to obtain a biological self-assembled nanocrystal freeze-dried powder for injection, which can be administered by interstitial injection after hydration and shaking prior to use.

The biological self-assembled nanocrystal powder injection prepared from the formulation and process had collapse and shrinkage in the surface after freeze-drying. After the hydration with water for injection, the mitoxantrone acetate injection was formed, which comprised mitoxantrone acetate in a concentration of 0.52% and had a pH determined to be 3.5 and osmotic pressure of 1503 mmol/Kg. The self-assembled nanocrystals under the interstitial biological conditions had a particle size of 60 nm. The first, second, and third classes of metastatic lymph nodes after subcutaneous interstitial administration produced a dark blue color visible to naked eyes. The weight and volume of metastatic lymph nodes of each class decreased significantly or returned to normal and there was no significant toxicity for the injection site or the lymphocytes.

In the present application, the 1000 injections mean the injection prepared was separated into 1000 parts.

Comparative Example 1

The formulation of small-volume aqueous biological self-assembled nanocrystal injection and the amounts of components for 1000 injections were as follows:

| | |
|---|---|
| Mitoxantrone hydrochloride | 0.23 g |
| Acetic acid | 0.52 g |
| Sodium acetate | 0.40 g |
| Disodium edetate | 0.10 g |
| Water for injection | 2000 mL |
| Activated carbon (used in the process and finally removed) | 2 g |

An appropriate amount of raw materials and excipients were weighed. 70% of the prescribed amount of water for injection was added to a concentrated mixing tank. The prescribed amount of excipients were added and dissolved by stirring for about 15 minutes. Then, mitoxantrone hydrochloride was added and dissolved by stirring for about 20 minutes. The activated carbon was fed and stirred for adsorption for 20 minutes at 40 to 60° C. The concentrated solution was filtered through a 3 µm stainless steel pleated cartridge filter and transferred into a dilution tank, supplemented with water for injection to the total amount of the solution to be prepared and stirred for 10 minutes. The drug solution was filtered through two sterilizing filters (with pore size of 0.22 µm) in series, aseptically and separately filled, and sealed.

The small-volume aqueous biological self-assembled nanocrystal injection prepared from the formulation and process comprised mitoxantrone hydrochloride in a concentration of 0.01%, and had a pH determined to be 6.83 and osmotic pressure of 196 mmol/Kg. Only the first class of metastatic lymph nodes after subcutaneous interstitial administration produced a light blue color which was hard to discern for naked eyes. The weight and volume of metastatic lymph nodes of each class were not significantly affected.

Comparative Example 2

The formulation of small-volume aqueous biological self-assembled nanocrystal injection and the amounts of components for 1000 injections were as follows:

| Mitoxantrone hydrochloride | 232.8 g |
|---|---|
| Acetic acid | 1.52 g |
| Sodium acetate | 0.10 g |
| Disodium edetate | 0.10 g |
| Water for injection | 2000 mL |
| Activated carbon (used in the process and finally removed) | 2 g |

An appropriate amount of raw materials and excipients were weighed. 70% of the prescribed amount of water for injection was added to a concentrated mixing tank. The prescribed amount of excipients were added and dissolved by stirring for about 15 minutes. Then, mitoxantrone hydrochloride was added and dissolved by stirring for about 20 minutes. The activated carbon was fed and stirred for adsorption for 20 minutes at 40 to 60° C. The concentrated solution was filtered through a 3 µm stainless steel pleated cartridge filter and transferred into a dilution tank, supplemented with water for injection to the total amount of the solution to be prepared and stirred for 10 minutes. The drug solution was filtered through two sterilizing filters (with pore size of 0.22 µm) in series, aseptically and separately filled, and sealed.

The small-volume aqueous biological self-assembled nanocrystal injection prepared from the formulation and process comprised mitoxantrone hydrochloride in a concentration of 10.34%, and had a pH determined to be 1.66 and osmotic pressure of 196 mmol/Kg. The self-assembled nanocrystals under the interstitial biological conditions had a particle size of 120 nm. The first, second, and third classes of metastatic lymph nodes after subcutaneous interstitial administration produced a dark blue color visible to naked eyes. The weight and volume of metastatic lymph nodes of each class decreased significantly or returned to normal, but there was significant toxicity for the injection site and the lymphocytes.

Control Example

1. Preparation of the Control Solution

An Isosulfan Blue solution (IB) was selected as the control solution. The formulation and preparation process were as follows:

Formulation:

| IB (drug substance) | 10 g |
|---|---|
| Disodium hydrogen phosphate (buffer) | 6.6 g |
| Potassium dihydrogen phosphate (buffer) | 2.7 g |
| Sodium chloride (osmotic pressure regulator) | 20 g |
| Water for injection added to For 200 injections | 1000 mL |

Preparation Process:

A prescribed amount of disodium hydrogen phosphate, potassium dihydrogen phosphate, and sodium chloride were weighed, added with 80% of the prescribed amount of water for injection, and dissolved by stirring for about 15 minutes. Then, a prescribed amount of IB was added and dissolved by stirring for about 20 minutes. The pharmaceutical carbon was fed and stirred for adsorption for 20 minutes at 50° C. The concentrated solution was filtered through a 3 µm carbon rod and transferred into a dilution tank with rinsing, and the rinsing fluid was combined into the solution. Water for injection was supplemented to the prescribed volume of drug solution in the dilution tank, and stirred for about 10 minutes. Sample was taken for the test of characters, pH and content. The drug solution that passed the intermediate test was filtered through a 0.22 µm microporous membrane, and sampled for the test of visible foreign matters. The drug solution that passed the test of visible foreign matters was purged with nitrogen, filled and sealed for 5.1±0.1 mL per dose, and sterilized for 15 minutes at 121° C. The finished product was obtained after leak detection, light inspection, labeling, and packaging.

2. Preparation of the Control Nano-Formulation

A mitoxantrone hydrochloride liposome (MIH-LIP) was selected as the control nano-formulation. The formulation and preparation process were as follows:

Formulation:

| Mitoxantrone hydrochloride | 4% | |
|---|---|---|
| Soy lecithin | 400 | mg |
| Cholesterol | 100 | mg |
| Phosphate buffer of pH 7.4 | 30 | mL |

Preparation Process:

The MIH-LIP was prepared by the thin film method: the soy lecithin and cholesterol were respectively weighed and dissolved in 5 mL of anhydrous ether; the anhydrous ether was completely removed by rotary evaporation under vacuum; an appropriate amount of phosphate buffer was added to hydrate to obtain a uniform light yellow emulsion; the emulsion was transferred into a polypropylene centrifuge tube; and the tube was placed in an ice bath for ultrasonic treatment with a probe for 3 minutes (working for 50 s and resting for 10 s). The light yellow translucent liquid was poured into a round-bottom flask containing the weighed mitoxantrone hydrochloride, and subjected to rotary evaporation at 37° C. to produce a uniform blue-black colloidal solution, reserved at 4° C. for use.

3. Particle Size Determination

Physiological saline was used to simulate the physiological environment in vivo, and the mitoxantrone hydrochloride biological self-assembled nanocrystal injection (MIH-Injection) was placed in the physiological environment to test the self-assembling under biological conditions using the particle size as an indicator. Mitoxantrone hydrochloride (MIH) is special, and traditional particle size determination means such as Malvern particle size analyzer cannot accurately determine its particle size range, while transmission electron microscope and other determination methods require dry samples for determination and cannot completely simulate the real self-assembled morphology in the in vivo environment. Therefore, the atomic force microscope was selected to characterize the morphology of its self-assembled nanoparticles under physiological conditions. It turned out that MIH could self-assemble into nanoparticles with a particle size of about 60 nm under physiological conditions, and the nanoparticles showed a round and integral morphology, a uniform dispersion, and a consistent particle size. Under acidic conditions, the particle size was about 10 nm.

4. Determination of the IB Particle Size

According to the above method, the same concentration of IB solution was placed under physiological conditions, and its particle size and morphology were determined by atomic force microscopy. The test results showed that under physiological conditions the individual IB particles had a uniform particle size from 10 nm to 20 nm and a round and integral morphology.

5. Determination of the MIH-LIP Particle Size

The particle size of the control formulation MIH-LIP was determined using a Malvern particle size analyzer. The test results showed that the particle size of MIH-LIP was about 140 nm.

6. Investigation of the pH Value 6.1. Effect of pH on the Drug Stability

Mitoxantrone hydrochloride was used as a model drug. The pH of the injection was adjusted to 1.5, 2.0, 2.5, 3.5, 4.5, 5.5, 6.0, 6.5, and 7.0, respectively. At one hour after adjusting the pH value, the content of the drug was determined after filtration through a 0.22 μm membrane. When the pH was between 1.5 and 6.0, the drug content was from 98.45±0.61% to 101.72±0.20%. When the pH was 6.5 and 7.0, the drug content significantly decreased to 83.76±0.53% and 75.38±0.22%, respectively. It indicated that when the pH of the injection was greater than 6.0, the drug in the injection was unstable and precipitated.

6.2. Effect of pH on the Drug Targeting Ability

Mitoxantrone hydrochloride was used as a model drug. The pH of the injection was adjusted to 1.5, 2.0, 2.5, 3.5, 4.5, 5.5, and 6.0, respectively. The mode of administration of interstitial injection was selected for subcutaneous injection in the paws of Kunming mice. At the pre-set time points, the mice were sacrificed by cervical dislocation, and the first, second and third classes of lymph nodes of the mice were removed for observation of staining. When the pH was less than 2.0, only one class of lymph nodes could be stained. When the pH was between 2.0 and 6.0, the three classes of lymph nodes could be stained; however, when the pH was 2.0, 2.5 or 6.0, the third class of lymph nodes were light blue, while all the three classes of lymph nodes could be stained into dark blue when the pH was between 3.5 and 5.5.

7. Investigation of the Osmotic Pressure 7.1. Effect of the Osmotic Pressure on the Irritation of the Injection Site Mitoxantrone hydrochloride was used as a model drug. The osmotic pressure of the injection was adjusted to 112, 196, 285, 307, 1503, 2317, and 3011 mmol/Kg, respectively. The mode of administration of interstitial injection was selected for subcutaneous injection in the paws of Kunming mice. At the pre-set time points, the mice were sacrificed by cervical dislocation, and the administration sites of the mice were taken for H&E staining to evaluate local irritation. When the osmotic pressure of the injection was 3011 mmol/Kg, redness and swelling occurred and the H&E staining showed local irritation, while other osmotic pressure values did not show obvious local irritation.

7.2. Effect of the Osmotic Pressure on the Drug Targeting Ability

Mitoxantrone hydrochloride was used as a model drug. The osmotic pressure of the injection was adjusted to 112, 196, 285, 307, 1503, 2317, and 3011 mmol/Kg, respectively. The mode of administration of interstitial injection was selected for subcutaneous injection in the paws of Kunming mice. At the pre-set time points, the mice were sacrificed by cervical dislocation, and the first, second and third classes of lymph nodes were removed for observation of staining. When the osmotic pressure was less than 285 mmol/Kg, only one class of lymph nodes could be stained. When the osmotic pressure was between 285 and 2317 mmol/Kg, all the three classes of lymph nodes could be stained; however, when the osmotic pressure was 285 or 2317 mmol/Kg, the third class of lymph nodes were light blue, while all the three classes of lymph nodes could be stained into dark blue when the osmotic pressure was between 307 and 1503 mmol/Kg.

8. Investigation of the Lymphatic Targeting Ability after Interstitial Administration The lymphatic targeting ability of this novel biological in vivo self-assembled nano-drug delivery system was investigated. The mode of administration of interstitial injection was selected for subcutaneous injection of 20 μL of the mitoxantrone hydrochloride biological self-assembled nanocrystal injection (MIH-Injection) in the paws of Kunming mice. At the pre-set time points, the mice were sacrificed by cervical dislocation, and the first, second and third classes of lymph nodes of the mice were removed for observation of staining and the content of MIH in the lymph nodes was determined by HPLC. According to the test results, it was known from the area under the drug concentration-time curve (AUC) and the maximum peak concentration (Cmax) that the MIH-Injection by interstitial administration had a good targeting effect for the first class of lymph nodes (PLNS), the second class of lymph nodes (ILNS) and the third class of lymph nodes (RLNS), and with reference to the drug content in the blood (no drug was detected in the blood), the targeting efficiency could reach 100%, that is, the particle size after self-assembling by interstitial administration could enable all the particles to enter the lymphatic system without entry into the blood circulation.

TABLE 1

Pharmacokinetics parameters in lymph nodes after subcutaneous injection of MIH-Injection

| data | MIH-Injection | | |
| --- | --- | --- | --- |
| | PLNs | ILNs | RLNs |
| AUC(mg · h/kg) | 3102.01 ± 151.21 | 2249.78 ± 109.71 | 963.89 ± 98.13 |
| Cmax(mg/kg) | 221.12 ± 35.55 | 157.56 ± 21.43 | 373.86 ± 16.92 |

Note:
PLNs: popliteal lymph nodes
ILNs: iliac lymph nodes
RLNs: renal lymph nodes
AUC (area under the drug concentration-time curve)
Cmax (maximum peak concentration)

At the same time, IB and MIH-LIP were used as control formulations to explore the effect of different particle sizes on the lymphatic targeting ability of the drug delivery system. IB (20 nm), MIH-Injection (60 nm) and MIH-LIP (130 nm) were administered by interstitial injection. The test results at two hours after the injection were shown in Table 2 below. It was shown that the mitoxantrone hydrochloride biological self-assembled nanocrystals provided the drug molecules of mitoxantrone hydrochloride with a certain particle size, making them have a lymphatic targeting ability superior to the liposome and the conventional injections.

TABLE 2

Lymphatic targeting abilities of formulations with different particle sizes
Concentration of drug accumulated in lymph nodes (ng/mL)

| PLNs | | | ILNs | | | RLNs | | |
|---|---|---|---|---|---|---|---|---|
| 20 nm | 60 nm | 130 nm | 20 nm | 60 nm | 130 nm | 20 nm | 60 nm | 130 nm |
| 23.044 | 2137 | 1551.005 | 6.999 | 1455 | 1124.89 | 0.893 | 512 | 481.945 |

Note:
PLNs: popliteal lymph nodes
ILNs: iliac lymph nodes
RLNs: renal lymph nodes 9. Investigation of the Lymphatic Targeting Speed Nine Kunming mice were randomly divided into three groups: MIH-Injection group, MIH-LIP group, and IB group. Three mice in each group were subcutaneously administered in the paws. At 10 minutes after administration, the mice were sacrificed by cervical dislocation and dissected. The first, second and third classes of lymph nodes were taken and observed for staining effects. The test results showed that all the three classes of lymph nodes of the MIH-Injection group were stained to a darker color than the IB group and the MIH-LIP group, with good effects, in particular good lymph node tracing effects. MIH-Injection showed advantages over MIH-LIP in terms of lymph node tracing. The reason for this may be that the fluidity of the solution is better than that of the liposome.

10. Investigation of the Therapeutic Effect on Metastatic Lymph Nodes 10.1. Investigation of Inhibitory Effect of the Local Interstitial Administration on Lymphatic Metastasis Tumors Under the local administration regimen, the sizes of the first and second classes of lymph nodes of different phases were compared, and the mass and volume of the lymph nodes were investigated. The results were shown in Table 3. It can be concluded from analysis of the data that MIH-Injection had a significant inhibitory effect on lymphatic metastasis cancer, the volume and weight of each class of lymphatic metastasis tumor were significantly reduced, and its efficacy was related to the chemotherapy phase. The inhibitory effect of local administration of MIH-Injection on the second class of metastatic lymphoma did not significantly differ from the effect on the first class of metastatic lymphoma ($p>0.05$).

TABLE 3

Comparison of sizes of lymph nodes between different phases for the local injection group

| | MPLNs (mm$^3$, V) | MILNs (mm$^3$, V) | MPLNs (mg, m) | MILNs (mg, m) |
|---|---|---|---|---|
| Phase I | 5.48 | 1.61 | 5.19 | 1.55 |
| Phase II | 1.92 | 0.76 | 1.94 | 0.92 |
| Phase III | 4.26 | 0.92 | 2.97 | 1.03 |
| Phase IV | 2.45 | 1.00 | 3.35 | 0.89 |

Note:
Phase I: the first phase of chemotherapy
Phase II: the second phase of chemotherapy
Phase III: the third phase of chemotherapy
Phase IV: the fourth phase of chemotherapy
MPLNs: mestastatic popliteal lymph nodes
MILNs: mestastatic iliac lymph nodes
V: volume
m: mass 10.2. Comparison of the Inhibitory Effects of Local Administration and Intravenous Administration on Lymphatic Metastasis Tumors Different dosing regimens were designed to compare the therapeutic effects of local injection and intravenous injection of MIH-Injection on lymphoma in different phases. Experimental data for the local and intravenous administration groups are listed as follows. It can be concluded from these results that the local administration had a greater inhibitory effect on lymphoma and more rapid onset of efficacy as compared with the systemic intravenous injection.

TABLE 4

Comparison of lymph node sizes between the local and intravenous injection groups for different phases

| | Local injection group | | | | Intravenous injection group | | | |
|---|---|---|---|---|---|---|---|---|
| | MPLNs (mm$^3$,V) | MPLNs (mg, m) | MILNs (mm$^3$,V) | MILNs (mg, m) | MPLNs (mm$^3$,V) | MPLNs (mg, m) | MILNs (mm$^3$,V) | MILNs (mg, m) |
| Phase I | 5.48 | 5.19 | 1.95 | 1.55 | 8.05 | 9.32 | 2.85 | 2.01 |
| Phase II | 1.92 | 1.94 | 0.76 | 0.92 | 7.59 | 8.17 | 2.50 | 1.95 |
| Phase III | 4.26 | 2.97 | 0.92 | 1.03 | 8.00 | 3.51 | 2.00 | 1.64 |
| Phase IV | 2.45 | 3.35 | 1.00 | 0.89 | 2.78 | 3.90 | 1.25 | 1.03 |

Note:
Phase I: the first phase of chemotherapy
Phase II: the second phase of chemotherapy
Phase III: the third phase of chemotherapy
Phase IV: the fourth phase of chemotherapy
MPLNs: mestastatic popliteal lymph nodes
MILNs: mestastatic iliac lymph nodes
V: volume
m: mass The above description is only related to preferred specific embodiments of the present application, but the scope of protection of the present application is not limited thereto, and any person skilled in the art can within the technical scope disclosed in the present application easily think of changes or replacements, which should be covered by the scope of this application.

The invention claimed is:

1. A biological self-assembled nanocrystal injection having a lymphatic targeting function, characterized in that the components of the injection comprise 0.05% to 5% of mitoxantrone or a salt thereof, 0.1 to 10% of sodium chloride calculated by a mass-to-volume ratio (g/mL), 0.001 to 0.1% of sodium acetate, 0.01 to 0.1% of sodium metasulfite, with the remainder being a solvent,
characterized in that the pH range of the injection is from 3.5 to 5.5,
characterized in that the osmotic pressure of the injection ranges from 307 to 1503 mmol/Kg, and
characterized in that the injection is administered interstitially.

2. The biological self-assembled nanocrystal injection having a lymphatic targeting function according to claim 1, characterized in that the mitoxantrone or salt thereof is present in a concentration ranging from 0.1% to 1% in the injection.

3. The biological self-assembled nanocrystal injection having a lymphatic targeting function according to claim 1, characterized in that the salt of mitoxantrone is one or more selected from the group consisting of hydrochloride, oxalate, sulfate, phosphate, acetate, or citrate of mitoxantrone.

4. The biological self-assembled nanocrystal injection having a lymphatic targeting function according to claim 1, characterized in that the injection comprises a small-volume aqueous injection and a powder injection, with the small-volume aqueous injection containing no filler and the powder injection containing a filler in an amount of greater than 0 and less than or equal to 20%.

5. The biological self-assembled nanocrystal injection having a lymphatic targeting function according to claim 1, wherein the injection further comprises:
  0 to 20% of a filler, wherein the filler is one or more selected from the group consisting of a monosaccharide, selected from the group consisting of glucose, fructose, galactose, ribose, and deoxyribose, a disaccharose, selected from the group consisting of sucrose, trehalose, maltose, and lactose, and a polymeric sugar, selected from the group consisting of mannitol, sorbitol, lactitol, xylitol, maltitol, and erythritol; and
  0.05 to 1% of an adsorbent, wherein the adsorbent is activated carbon.

6. The biological self-assembled nanocrystal injection having a lymphatic targeting function according to claim 1, characterized in that after the lymphatic targeting function is realized, the lymph nodes produce a blue color visible to the naked eyes.

7. The biological self-assembled nanocrystal injection having a lymphatic targeting function according to claim 1, characterized in that after the lymphatic targeting function is realized, the tumor metastasis lymph nodes shrink or return to normal size.

8. The biological self-assembled nanocrystal injection having a lymphatic targeting function according to claim 1, characterized in that the administered injection is in the form of a solution, and the mitoxantrone or its salt is present in the form of completely dissolved molecules.

9. The biological self-assembled nanocrystal injection having a lymphatic targeting function according to claim 1, characterized in that after the injection in the form of a solution is administered interstitially, the nanocrystals are self-assembled in the injection site.

10. A preparation method of biological self-assembled nanocrystal injection having a lymphatic targeting function according to claim 1, characterized in that the injection is a small-volume aqueous biological self-assembled nanocrystal injection, and the method comprises the following preparation steps: weighing an appropriate amount of raw materials and excipients, adding 70% of the prescribed amount of water for injection to a concentrated mixing tank, adding the prescribed amount of excipients, stirring for about 15 minutes to dissolve, then adding mitoxantrone or a salt thereof, stirring for about 20 minutes to dissolve, feeding the activated carbon, stirring for adsorption for 20 minutes at 40 to 60° C., filtering the concentrated solution through a 3 μm stainless steel pleated cartridge filter and transferring it into a dilution tank, supplementing water for injection to the total amount of the solution to be prepared, stirring for 10 minutes, filtering the drug solution through two sterilizing filters with pore size of 0.22 μm in series, and aseptically and separately filling and sealing.

11. A preparation method of biological self-assembled nanocrystal injection having a lymphatic targeting function according to claim 1, characterized in that the injection is a biological self-assembled nanocrystal powder injection, and the method comprises the following preparation steps: weighing an appropriate amount of raw materials and excipients, adding 70% of the prescribed amount of water for injection to a concentrated mixing tank, adding the prescribed amount of excipients, stirring for about 15 minutes to dissolve, then adding mitoxantrone or a salt thereof, stirring for about 20 minutes to dissolve, feeding the activated carbon, stirring for adsorption for 20 minutes at 40 to 60° C., filtering the concentrated solution through a 3 μm stainless steel pleated cartridge filter and transferring it into a dilution tank, supplementing water for injection to the total amount of the solution to be prepared, stirring for 10 minutes, filtering the drug solution through two sterilizing filters with pore size of 0.22 μm in series, adding mannitol to be dissolved, and removing water by freeze-drying to obtain a biological self-assembled nanocrystal freeze-dried powder for injection, which can be administered by interstitial injection after hydration and shaking prior to use, with the hydration medium being one or more selected from the group consisting of water for injection, physiological saline, and glucose injection.

12. The biological self-assembled nanocrystal injection having a lymphatic targeting function according to claim 1, characterized in that the nanocrystal has a particle size from 30 nm to 60 nm under physiological conditions.

* * * * *